US007169137B2

(12) United States Patent
Shimada

(10) Patent No.: US 7,169,137 B2
(45) Date of Patent: Jan. 30, 2007

(54) ABSORBENT ARTICLE HAVING A DECORATIVE ELEMENT

(75) Inventor: Takaaki Shimada, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 0 days.

(21) Appl. No.: 11/042,197
(22) Filed: Jan. 26, 2005

(65) Prior Publication Data

US 2005/0131366 A1    Jun. 16, 2005

Related U.S. Application Data

(63) Continuation of application No. PCT/JP03/10993, filed on Aug. 28, 2003.

(30) Foreign Application Priority Data

Aug. 30, 2002 (JP) .............................. 2002-256073
Aug. 21, 2003 (JP) .............................. 2003-208297

(51) Int. Cl.
A61F 13/15 (2006.01)
(52) U.S. Cl. ..................... 604/385.29; 604/385.27; 604/385.23; 604/385.24; 604/385.26; 604/385.01
(58) Field of Classification Search ................ 604/367, 604/361, 362, 366, 385.01, 385.29, 385.27, 604/385.23, 385.24, 385.26
See application file for complete search history.

(56) References Cited

U.S. PATENT DOCUMENTS

2001/0006867 A1*    7/2001    Suekane et al. ............ 442/394

FOREIGN PATENT DOCUMENTS

| EP | 0 114 755 A2 | 8/1984 |
| EP | 1 110 527 A2 | 6/2001 |
| JP | 2002-000657 | 1/2002 |
| JP | 2002-011045 | 1/2002 |

\* cited by examiner

Primary Examiner—Jacqueline F. Stephens
(74) Attorney, Agent, or Firm—Lowe Hauptman & Berner LLP

(57) ABSTRACT

An absorbent article includes a chassis defining front and rear waist regions, an absorbent panel laid on the inner surface of the chassis and a decorative element adapted to be seen through the chassis and interposed between an intermediate zone of the chassis and the absorbent panel. An optical transmittance exhibited by the intermediate zone of the chassis in which the decorative element is laid is higher than an optical transmittance exhibited by opposite lateral zones of the chassis.

4 Claims, 6 Drawing Sheets

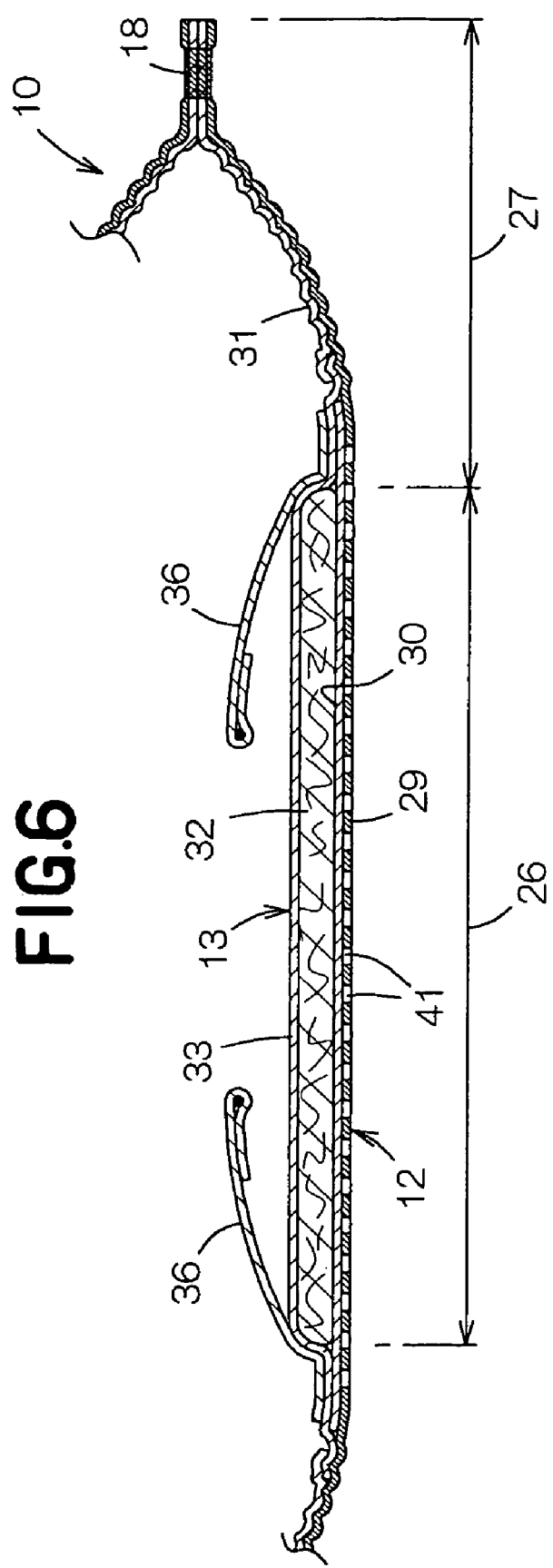

ABSORBENT ARTICLE HAVING A DECORATIVE ELEMENT

This application is a continuation of International Application No. PCT/JP2003/010993 filed Aug. 28, 2003, which claims priority to Japanese Application Nos. 2002-256073 filed on Aug. 30, 2002 and 2003-208297 filed Aug. 21, 2003, all of which are hereby incorporated by reference herein in their entirety.

BACKGROUND OF THE INVENTION

The present invention relates to an absorbent article provided with a decorative element and more particularly to disposable pull-on diaper, open-type diaper, training pants, incontinence pants and the analogous articles provided with the decorative element such as picture, letters or symbols displayed in a waist region of the article.

Japanese Laid-Open Patent Application Publication No. 2002-657A discloses an absorbent article such as a disposable diaper comprising a fibrous nonwoven fabric exhibiting an optical transmittance of 40 to 83% as the outermost sheet constituting an outer sheet of the article in order to ensure cloth-like appearance and touch and film printed with multicolored picture and fixed to the inner surface of the above-mentioned nonwoven fabric so that the picture can be seen through the nonwoven fabric.

The decorative element such as picture should be seen through the outer sheet as clearly as possible in order to improve its design effect and this can be achieved by improving an optical transmittance of the fibrous nonwoven fabric used as the outer sheet adapted to cover the decorative element from outside. However, higher the optical transmittance of the nonwoven fabric, higher a see-through clarity of the nonwoven fabric is. In consequence, the wearer's body would be too distinctively seen through the nonwoven fabric. If fibrous nonwoven fabric exhibiting a relatively low optical transmittance is used to avoid this inconvenience, the see-through clarity for the decorative element would be unacceptably deteriorated. In this manner, selection of the optical transmittance to be exhibited by the fibrous nonwoven fabric constituting the outermost surface of the article necessarily encounters a problem of antinomy.

SUMMARY OF THE INVENTION

It is an object of the present invention to solve the problem as has been described above by differentiating the optical transmittance in a zone of the outer sheet in which the decorative element is laid and covered with the outer sheet and in opposite lateral zones of the article in which the wearer's body is apt to be seen through the outer sheet.

The present invention relates to an absorbent article comprising at least a flexible chassis defining front and rear waist regions opposed to each other when the article is put on the wearer's body and a crotch region extending between these front and rear waist regions, a semi-rigid absorbent member laid on an inner surface of the chassis and having a decorative element adapted to be seen through the chassis and laid on at least one of the front and rear waist regions. The article further comprises the chassis having an intermediate zone and opposite lateral zones, and the intermediate zone exhibits an optical transmittance higher than an optical transmittance exhibited by the opposed lateral zones.

To ensure that the optical transmittance of the chassis in the intermediate zone is higher than that in the opposite lateral zones, it is preferred to adopt any one of the embodiments as will be described. Assumed that the intermediate zone of the chassis in which the decorative element is laid and the opposed lateral zones are formed by fibrous nonwoven fabric, the number of nonwoven fabric layers in the intermediate zone may be selected to be fewer than the number of nonwoven fabric layers in the opposed lateral zones. Alternatively, a fiber density in the opposed lateral zones may be adjusted to be higher than a fiber density in the intermediate zone. As further alternative embodiment, at least a part of the intermediate zone in which the decorative is laid may be provided with a means for increasing the optical transmittance. Examples of the means include making a plurality of perforations, a treatment using a heat roll to convert the fibers to a filmy state and a treatment using a liquid wax, a liquid paraffin or a solvent.

The nonwoven fabric may be selected from those of conventional thermoplastic synthetic fibers. While the decorative element may be displayed on the conventional thermoplastic film or the conventional fibrous nonwoven fabric, it is preferred to use the nonwoven fabric having a fiber density and a surface smoothness higher than the nonwoven fabric constituting the chassis as well as the nonwoven fabric covering the absorbent panel in view of an effect to display the decorative element.

The decorative element may be, for example, a picture of any popular characters, letter(s) or symbol(s) or combination of at least two thereof. The manner of displaying this element may be two-dimensional or three-dimensional manner. The decorative element may be multiple-colored or single-colored so far as the color of the decorative element is different from the color of the nonwoven fabric constituting the outer surface of the chassis.

The other features of the invention regarding construction and materials will be understood from the description of preferred embodiments given hereunder. However, the present invention is not limited to these embodiments.

BRIEF DESCRIPTION OF THE DRAWINGS

FIG. 6 is a transverse sectional view similar to FIG. 2 showing the article of FIG. 5.

DETAILED DESCRIPTION OF THE PREFERRED EMBODIMENTS

The present invention will be more fully understood from the description of several embodiments given hereunder with reference to the accompanying drawings.

(First Embodiment)

Figure 1:
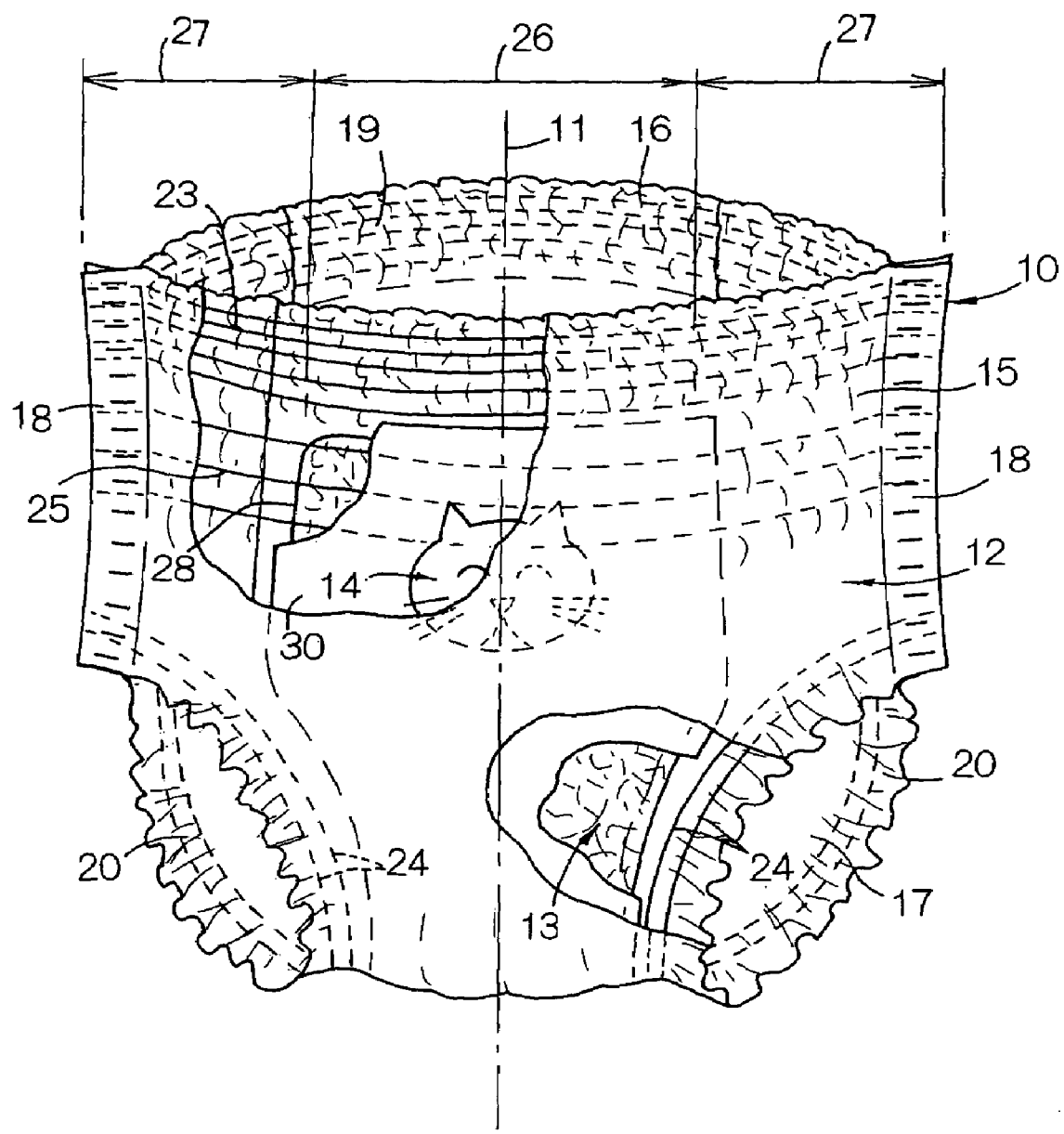
FIG. 1 is a partially cutaway perspective view showing a first embodiment of an article according to the invention.
Figure 2:
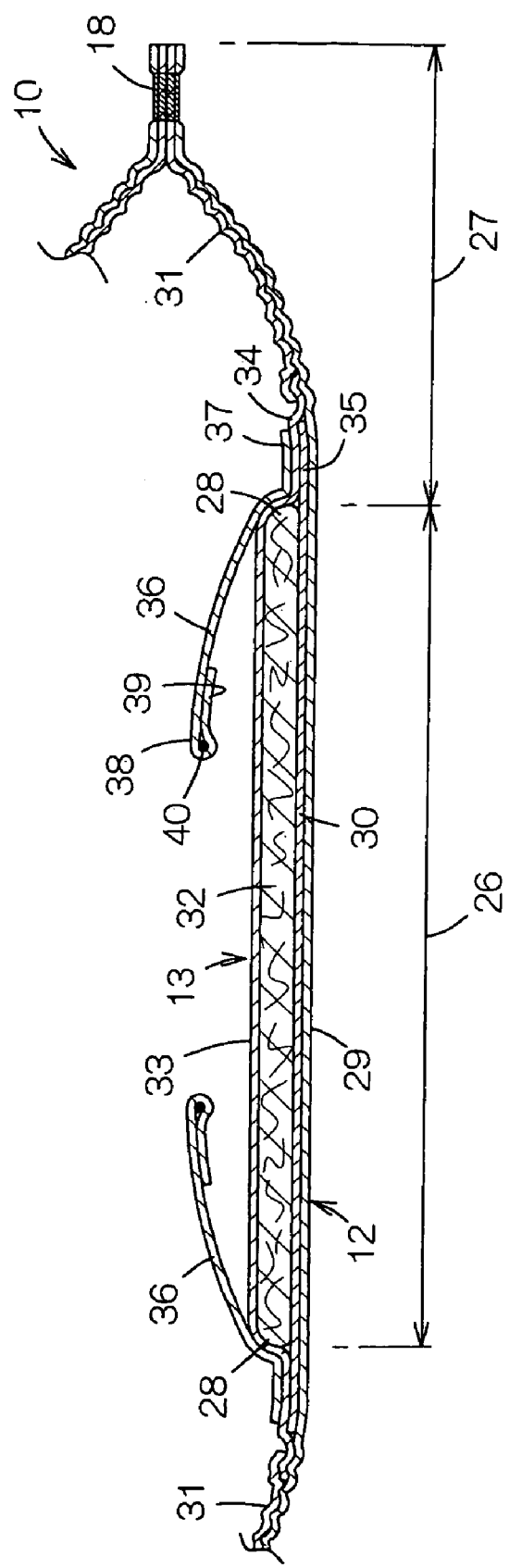
FIG. 2 is a transverse sectional view showing a part of the article.

FIGS. 1 and 2 illustrate an absorbent article 10 as a first embodiment of the invention. As shown, the absorbent article 10 is symmetric about a longitudinal center line 11 and comprises a flexible chassis 12, a semi-rigid absorbent panel 13 laid on an inner surface of the chassis 12 and a decorative element 14 displayed on the chassis 12.

The chassis 12 defines a front waist region 15, a rear waist region 16 and a crotch region 17 in which the front and rear waist region 15, 16 respectively have lateral marginal zones 18 opposed to each other, along which these waist regions 15, 16 are intermittently joined together to form a pants-like configuration having a waist-hole 19 and a pair of leg-holes 20. As viewed in a developed state of the chassis 12 with the respectively opposed lateral marginal zones 18 disconnected from one another, the crotch region 17 describes substantially circular arcs which are convex toward the longitudinal center line 11. In other words, the chassis 12 has a substantially hourglass-like shape in this developed state. It should be understood that the article 10 may be configured in non-pants-type without departing from scope and spirit of the present invention.

The waist-hole 19 and the leg-holes 20 are provided in a circumferential direction of these holes 19, 20 with a plurality of elastic members 23, 24, respectively, secured to the chassis 12 in a stretched state. These elastic members 23, 24 are elastically contractible to hold peripheries of these waist- and leg-holes 19, 20 in close contact with wearer's waist and thighs and thereby to prevent an anxiety that the article 10 might unintentionally slip down along the wearer's waist and/or thighs and bodily discharges might leak beyond the peripheries of the waist- and leg-holes 19, 20. Between the waist- and leg-holes 19, 20, the chassis 12 is further provided in the front and rear waist regions 15, 16 with a plurality of elastic members 25 secured to the chassis 12 in a stretched state. These elastic members 25 extend across the absorbent panel 13 in the vicinity of longitudinally opposite ends thereof and serve to keep the absorbent panel 13 in contact with a wearer's body under a relatively moderate pressure. A contractile force of the elastic members 25 exhibited after the elastic members 25 have been stretched by a given amount within an elastic limit is lower than those exhibited by the elastic members 23, 24. These elastic members 25 are let free from the chassis 12 except for longitudinally opposite ends of these elastic members 25 fixed to the lateral marginal zones 18 of the chassis 12. With a consequence, the contractile force of the elastic members 25 affects only transversely opposite lateral zones 27 of the chassis 12 which will be described below more in detail so that gathers are formed in the lateral zones 27 while it does not affect the absorbent panel 13 and intermediate zone 26 of the chassis 12 which will be also described below more in detail.

Taking account of a position-relationship with the absorbent panel 13, the chassis 12 can be divided into the intermediate zone 26 and the opposite lateral zones 27. The intermediate zone 26 is substantially defined between transversely opposite side edges 28 thereof and each of the lateral zones 27 is substantially defined between each of the side edges 28 and the lateral zone 18. The chassis 12 comprises a hydrophobic outer sheet 29 which is identical to the chassis 12 in shape as well as in size, a moisture-permeable liquid barrier sheet 30 extending in the intermediate zone 26 in a longitudinal direction and a pair of hydrophobic side sheets 31 extending in the respective lateral zones 27 in the longitudinal direction.

The outer sheet 29 and the side sheets 31 are formed by a well known nonwoven fabric of thermoplastic synthetic fiber having a fineness of 0.8 to 5.0 dtex, preferably of 1.0 to 4.0 dtex and a basis weight of 10 to 35 g/m², preferably of 15 to 25 g/m² in which the thermoplastic synthetic fiber is oriented at random. The synthetic fiber may be selected from the group including polyolefine-, polyester- and polyamide-based fibers. The nonwoven fabric may be selected from the group including an air-through nonwoven fabric, a point bond nonwoven fabric, a melt bond nonwoven fabric, a spun bond nonwoven fabric and SMS.

The liquid barrier sheet 30 is formed by a well known thermoplastic film having a basis weight of 10 to 40 g/m². This film may be made, for example, of polyolefine-based synthetic resin. A decorative element 14 is displayed on an outer surface of the liquid barrier sheet 30. The liquid barrier sheet 30 may comprise the fibers similar to those of said nonwoven fabric so far as these fibers have a fiber density and a surface smoothness allowing the decorative element 14 to be printed thereon. It is preferable that such fiber density and surface smoothness are considerably higher than those of the nonwoven fabric used as the stock material for the outer sheet 29 and the side sheets 31.

The decorative element 14 may be, for example, a picture of any popular characters, letter(s) or symbol(s) or combination of at least two thereof. The decorative element 14 may be displayed on the liquid barrier sheet 30 preferably by two- or three-dimensionally printing the decorative element 14 using multiple colors or single color different from the color of the outer sheet 29.

The outer sheet 29 preferably has an optical transmittance of 40% or higher, more preferably of 70% or higher in order that the decorative element 14 can be clearly seen through the outer sheet 29. In the intermediate zone 26 of the chassis 12, only the outer sheet 29 is opposed to the liquid barrier sheet 30. In each of the lateral zones 27 of the chassis 12, on the other hand, the outer sheet 29 and the side sheet 31 laminated therewith are opposed to the liquid barrier sheet 30. While the optical transmittance in the lateral zone 27 of the side sheet 31 may be equal to or higher or lower than that of the outer sheet 29, this optical transmittance is lower than that of the outer sheet 29 in the intermediate zone 26 in view of the fact that component fibers in these two sheets laminated with each other are oriented at random. In this way, it is not likely that the wearer's body might be distinctly seen through the lateral zones 27.

It was experimentally found by the inventors that the optical transmittance of the chassis 12 in the intermediate zone 26 is preferably 70% or higher while the optical transmittance of the chassis 12 in the lateral zones 27 is preferably less than 70% in order to ensure a desired see-through clarity for the decorative element 14, to prevent the wearer's body from being distinctly seen and to simplify a construction of the chassis 12. While it is preferred to adjust the optical transmittance of the chassis 12 in the lateral zones 27 to a value as low as possible so far as the see-through clarity for the wearer's body is concerned, lower the optical transmittance is, higher the basis weight, the density and therefore the stiffness are. High stiffness is undesirable in view of properties of the article such as texture, touch and fitness.

Based on the above-mentioned findings, it is essential that the optical transmittance of the chassis 12 except for the liquid barrier sheet 30 is higher in the intermediate zone 26 than in the opposite lateral zones 27. So far as such essential condition is met, it is preferred that both the intermediate zone 26 and the opposite lateral zones 27 exhibit the optical transmittance approximate to 70% from the viewpoints of the see-through clarity and the construction of the chassis 12 as have been described. To meet such preferred condition with the optical transmittance of the intermediate zone 26 and the lateral zones 27 being maintained approximate to one another, the portion of the outer sheet 29 extending in the intermediate zone 26 is substantially kept in close contact with the liquid barrier sheet 30 displaying the decorative element 14 so that this portion of the outer sheet 29 may be protected from formation of gathers due to contraction of the elastic members 23, 24, 25, on one hand, and the opposite lateral zones 27 may be formed with gathers as the elastic members 23, 24, 25, particularly the elastic members 25 contract, on the other hand. The gathers formed on the lateral zones 27 of the article 10 put on the wearer's body further reduce the optical transmittance of the lateral zones 27 and thereby prevent the wearer's body from being distinctly seen through these lateral zones 27. The article 10 according to the first embodiment of the invention illustrated in FIG. 1 is constructed just in this manner. To keep the portion of the outer sheet 29 extending in the intermediate zone 26 in close contact with the liquid barrier sheet 30, these two sheets are preferably joined together by adhesion or heat-sealing. Preferably, these two sheets are intermittently bonded by adhesion or heat-sealing in appropriate pattern, for example, dot-pattern, line-pattern or spiral pattern in order to prevent moisture-permeability and flexibility of the outer sheet 29 and the liquid barrier sheet 30 deteriorating. Similarly, the portion of the outer sheet 29 and the associated side sheet 31 are intermittently joined together in the opposite lateral zones 27 by adhesion or heat-sealing. It should be noted here that a density of joining may be lower than that in the intermediate zone 26 because it is not essential to keep the outer sheet 29 and the side sheets 31 in close contact with one another. The density of joining is preferably low to improve texture and touch of the article 10.

The optical transmittance refers to a total transmittance measured according to the general optical characteristic transparency examination measuring method A, JIS (Japanese Industrial Standard) K7105 using a turbidity meter of the type NDH-300A, manufactured by Nippon Denshoku Kogyo Co., Ltd. as the measuring apparatus.

Details of the Measuring Method
(1) Preparing a test sample of a size 50 mm×50 mm
(2) Setting a piece of the sample to be held by clip for setting the sample on the measuring apparatus
(3) Pushing a start key of the measuring apparatus to start the measurement
(4) Measuring of Tt: a total transmittance (%) as the optical transmittance
(5) Taking an average of the measured values of three pieces of the sample Points of Concern
(1) The power supply of the measurement apparatus is turned ON 30 minutes or more before measuring.
(2) If a size of a sample is less than 50 mm×50 mm, the sample having a size more than 35 mm×35 mm is available as long as a surface of a measuring part on the measuring apparatus can be completely covered by the sample.
(3) It should be checked if a sample is correctly held by the clip for setting the sample or not especially when the sample is very flexible.
(4) A sheet to be tested is obtained by cutting out a part of a chassis from an absorbent article with scissors, etc. When the chassis is attached to other parts of the article by means of adhesives, etc, a sample can be obtained by removing carefully with the hot wind as long as the wind does not influence the optical transmittance of the chassis. Moreover, if the hot wind influences in the optical transmittance of the chassis, a sample can be obtained by drying after the melting adhesives with organic solvents, such as toluene.

The absorbent panel 13 comprises an hourglass-shaped liquid-absorbent core 32 which is substantially thicker than the nonwoven fabric as described above and a liquid-pervious cover sheet 33 adapted to cover the surface of the core 32 facing the wearer's body and a peripheral portion of the core 32. The core 32 comprises a mixture of fluff pulp and super-absorbent polymer particles or, if desired, a mixture of fluff pulp, super-absorbent polymer particles and thermoplastic synthetic fibers, in both cases, wrapped with a liquid-diffusive sheet such as a tissue paper for the primary purpose of preventing the core 32 from getting out of shape and compressed to a desired thickness. Taking account of such construction, it is possible to say that the core is rather semi-rigid than otherwise. Such core 32 is disposed on an upper surface of the liquid barrier sheet 30 leaving a peripheral margin free by an appropriate dimension. To avoid unintentional shift of the core 32 relative to the liquid barrier sheet 30, it is preferred to attach the core 32 intermittently to the liquid barrier sheet 30 by means of adhesive distributed in an appropriate pattern such as dot-pattern, line-pattern or spiral-pattern. A peripheral portion 34 of the cover sheet 33 extending outward beyond a peripheral edge of the core 32 extends further outward beyond a peripheral edge 35 of the liquid barrier sheet 30 and is joined to the outer sheet 29 in each of the opposite lateral zones 27. It is sufficient for the liquid barrier sheet 30 to have a size enough to cover a lower surface of the core 32 since the liquid barrier sheet 30 functions also to prevent bodily discharges once having been absorbed by the core 32 from leaking out. The transversely opposite side edges 28 of the core 32 have no need to extend into the lateral zones 27, so a moisture-permeability of these lateral zones 27 is not affected by the opposite side edges 28 of the core 32. While the liquid barrier sheet 30 also is moisture-permeable, the liquid barrier sheet 30 is generally provided with a plurality of fine perforations by drawing resinous composition containing an inorganic filler and the moisture-permeability thereof is lower than that exhibited by the nonwoven fabric constituting the outer sheet 29, the side sheets 31 and the cover sheet 33.

The article 10 further includes a pair of liquid barrier cuffs 36. Each of the liquid barrier cuffs 36 has a proximal edge 37 and a distal edge 38. The proximal edge 37 is secured to the absorbent panel 13 along the associated side edge of the absorbent panel 13 by well known means such as adhesion or heat-sealing. Each of the cuffs 36 is folded back at the distal edge 38 to form a sleeve 39 within which an elastic member 40 is secured thereto in a stretched state in its longitudinal direction. With such arrangement, the liquid barrier cuffs 36 tend to rise above the respective proximal edges 37 as the elastic members 40 contract and thereby to prevent bodily discharges from leaking sideways of the article 10. The liquid barrier cuffs 36 are formed preferably by hydrophobic fibrous nonwoven fabric selected from the above-described well known types of nonwoven fabric. Though not illustrated, the side sheets 31 extending in the respective lateral zones 27 may be replaced by the liquid barrier cuffs 36 of which the respective proximal edges 37 further extend outward and these extensions are laminated on the outer sheet 29 in the respective lateral zones 27.

The elastic members 23 associated with the waist-hole 16, the elastic members 24 associated with the leg-holes 17 and the elastic members 25 associated with the front and rear waist regions are covered with a constituent of the article 10 in order to prevent these elastic members from coming in direct contact with the wearer's body. Specifically, most of the elastic members 23 are interposed between the chassis 12 and the cover sheet 33. Alternatively, a dimension by which the chassis 12 extends outward beyond each of the longitudinally opposite ends of the core 32 so that this extension may be folded back to form a sleeve within which the elastic members 23 are wrapped. The elastic members 24 are interposed between the chassis 12 and the respective side sheets 31. The elastic members 25 are interposed between the chassis 12 and the absorbent panel 13 in the intermediate zone 26 and between the chassis 12 and the respective side sheets 31 in the respective lateral zones 27.

(Second Embodiment)

Figure 3:
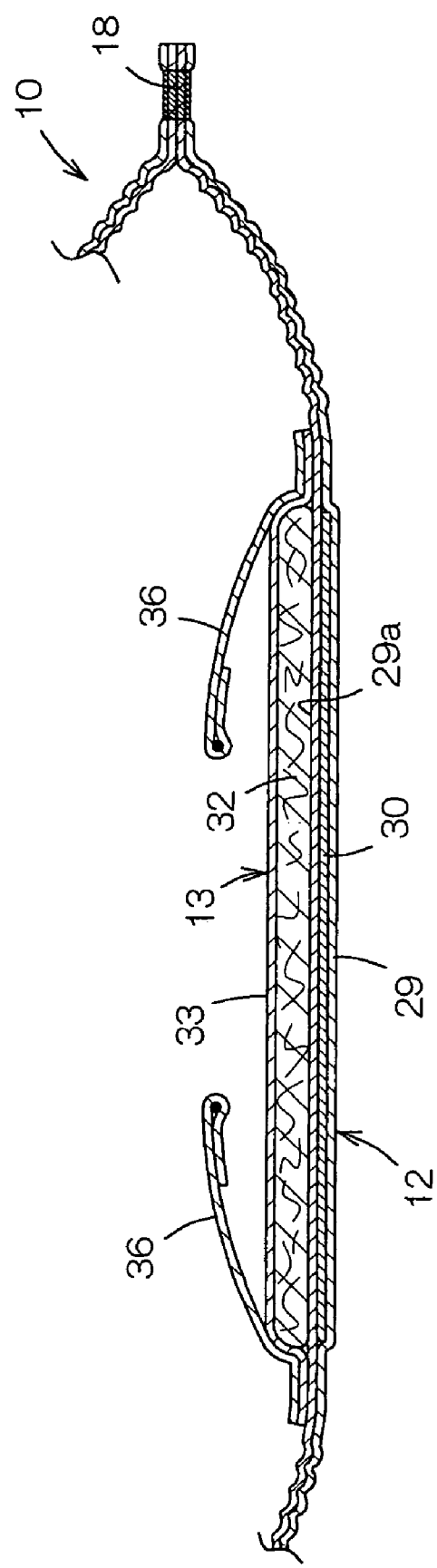
FIG. 3 is a transverse sectional view similar to FIG. 2 showing a second embodiment of the article according to the invention.

FIG. 3 shows a second embodiment of the article according to the invention. Of the article 10 according to this embodiment, the important members, portions and zones same as those in the article 10 according to the first embodiment are designated by the same reference numerals and will not be described in detail. The article 10 according to this embodiment is distinguished from that according to the first embodiment in that the chassis 12 comprises the inner and outer sheets 29a, 29 identical to each other in shape as well as in size and the liquid barrier sheet 30 interposed between these inner and outer sheets 29a, 29. In other words, the side sheets 31 separately provided in the respective lateral zones 27 in the article 10 according to the first embodiment are replaced by portions of the inner sheet 29a extending further into the respective lateral zones 27 in the article 10 according to this embodiment.

If desired, the portions of the inner and outer sheets 29a, 29 lying in the opposite lateral zones 27 may be compressed between a pair of heat rolls under heat and pressure adjusted so that the fibrous nonwoven fabric forming these sheets might not be molten. Thereby a fiber density in the opposite lateral zones 27 may become higher than that in the intermediate zone 26 to reduce the optical transmittance in the opposite lateral zones 27 compared to that in the intermediate zone 26.

Such treatment using the heat rolls is applicable to the opposite lateral zones 27 of the article according to the first embodiment, if desired.

(Third Embodiment)

Figure 4:
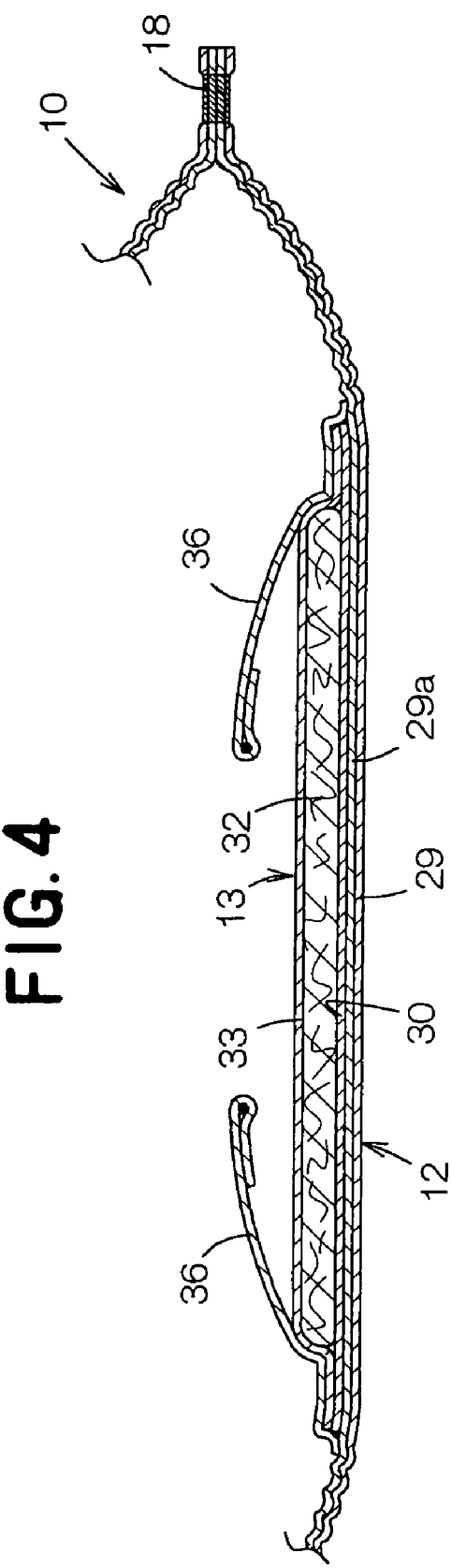
FIG. 4 is a transverse sectional view similar to FIG. 2 showing a third embodiment of the article according to the invention.

FIG. 4 illustrates a third embodiment of the article according to the invention. Of the article 10 according to this embodiment, the important members, portions and zones same as those in the article 10 according to the first embodiment are designated by the same reference numerals and will not be described in detail. The article 10 according to this embodiment is distinguished from that according to the first embodiment in that the chassis 12 comprises the inner and outer sheets 29a, 29 identical to each other in shape as well as in size, apart from the liquid barrier sheet 30. In other words, the side sheets 31 separately provided in the respective lateral zones 27 in the article 10 according to the first embodiment are replaced by portions of the inner sheet 29a extending further into the respective lateral zones 27 in the article 10 according to this embodiment.

In the article 10 according to this embodiment, the portions of the chassis 12 lying in the opposite lateral zones 27 are subjected to the above-described treatment. Specifically the inner and outer sheets 29a, 29 lying the opposite lateral zones 27 are compressed between a pair of heat rolls under heat and pressure adjusted so that the fibrous nonwoven fabric forming these sheets might not be molten and thereby a fiber density in the opposite lateral zones 27 is increased to a value higher than that in the intermediate zone 26 so as to reduce the optical transmittance in the opposite lateral zones 27 compared to that in the intermediate zone 26.

(Fourth Embodiment)

Figure 5:
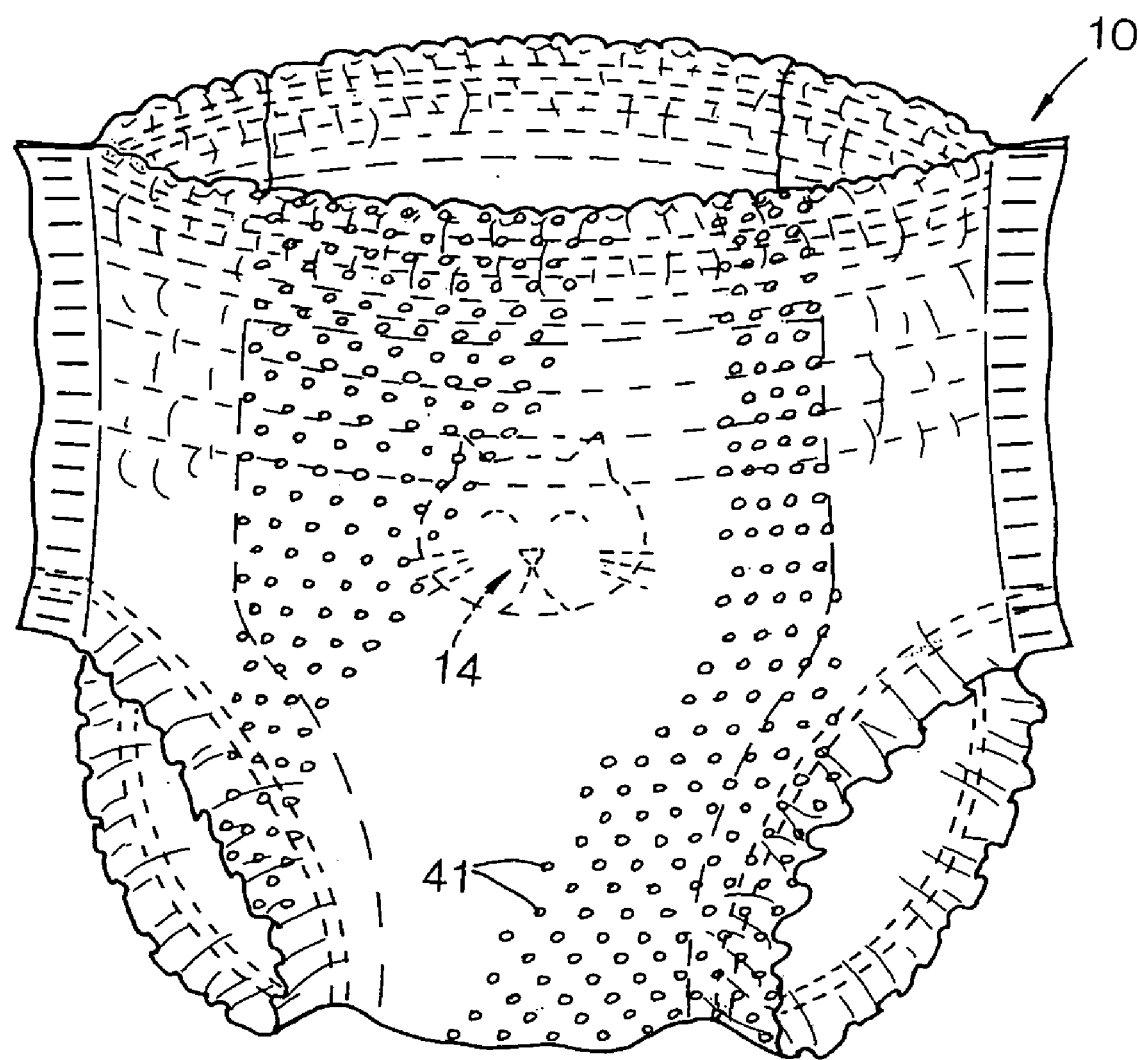
FIG. 5 is a perspective view similar to FIG. 1 showing a fourth embodiment of the article according to the invention.

FIGS. 5 and 6 illustrate a fourth embodiment of the article according to the invention. Of the article 10 according to this embodiment, the important members, portions and zones same as those in the article 10 according to the first embodiment are designated by the same reference numerals and will not be described in detail. The article 10 according to this embodiment is distinguished from the article 10 according to the first embodiment in that the outer sheet 29 constituting the chassis 12 is formed in its intermediate zone 26 with a plurality of perforations each having a diameter of 0.3 to 5 mm at an open area ratio of 30 to 70%. These perforations 41 are effective to increase the optical transmittance of the outer sheet 29 in the intermediate zone 26 and easily formed by the method of well known art.

(The Other Embodiments)

Though not illustrated, the optical transmittance can be differentiated between the intermediate zone 26 and the opposite lateral zones 27 of the chassis 12 by means other than the above-described means. Specifically, the nonwoven fabric in a part of the intermediate zone 26 displaying the decorative element 14 may be treated using a heat roll so that the fibers of the nonwoven fabric melt and thereby to convert the fibers to a filmy state or treated using a liquid max, a liquid paraffin or a solvent.

It should be understood that the embodiments as have been described hereinabove may be appropriately combined, if desired.

The article according to the present invention allows the decorative element lying in the intermediate zone of the chassis to be clearly seen through the article, on one hand, and prevents the wearer's body from being distinctly seen through the article, on the other hand. In this way, a high design effect is achieved and the above-described treatment to suppress the see-through clarity of the opposite lateral zones can be achieved without deterioration of texture, touch and fitness of the opposite lateral zones.

What is claimed is:

1. An absorbent article, comprising:
   a flexible chassis defining front and rear waist regions and a crotch region extending between said front and rear waist regions, said front and rear waist regions being joined together to form a waist-hole and a pair of leg-holes;
   an absorbent member more rigid than said chassis and bonded to on an inner surface of said chassis, said absorbent member having a decorative element adapted to be seen through said chassis and placed in at least one of said front and rear waist regions;
   said chassis having transversely opposite lateral zones and an intermediate zone between said lateral zones; and
   said intermediate zone having an optical transmittance higher than that of said lateral zones;
   wherein transversely extending elastic members are positioned in said waist regions and between said waist-hole and said leg-holes to extend across said decorative element without causing substantial contraction of said decorative element.

2. The article according to claim 1, wherein each of said elastic members provided in said waist regions is secured only at longitudinally opposite ends thereof to said opposite lateral zones of said chassis.

3. The article according to claim 2, wherein each of said elastic members further comprises a middle section located between and connecting said opposite ends;

said middle section being free of directed attachment to the intermediate zone of said chassis.

4. The article according to claim 3, wherein the lateral zones of said chassis comprise gathers caused by contraction of said elastic members, whereas the intermediate zone of said chassis, which is free of direct attachment to said elastic members, is substantially free of gathers.

\* \* \* \* \*